(12) United States Patent
Jagtap et al.

(10) Patent No.: US 10,150,745 B2
(45) Date of Patent: Dec. 11, 2018

(54) PROCESS FOR THE PREPARATION OF CLOBAZAM AND ITS INTERMEDIATE

(71) Applicant: PIRAMAL ENTERPRISES LIMITED, Maharashtra (IN)

(72) Inventors: Ashutosh Jagtap, Maharashtra (IN); Milind Gharpure, Maharashtra (IN); Navnath Shinde, Maharashtra (IN); Navnath Patil, Maharashtra (IN); Chirag Shah, Maharashtra (IN); Changdev Raut, Maharashtra (IN); Dhileepkumar Krishnmurthy, Maharashtra (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

(21) Appl. No.: 15/559,987

(22) PCT Filed: Mar. 21, 2016

(86) PCT No.: PCT/IB2016/051562
§ 371 (c)(1),
(2) Date: Sep. 20, 2017

(87) PCT Pub. No.: WO2016/151464
PCT Pub. Date: Sep. 29, 2016

(65) Prior Publication Data
US 2018/0065939 A1    Mar. 8, 2018

(30) Foreign Application Priority Data
Mar. 24, 2015   (IN) .......................... 966/MUM/2015

(51) Int. Cl.
| C07D 243/12 | (2006.01) |
| C07C 231/02 | (2006.01) |
| C07C 233/43 | (2006.01) |
| C07B 37/10  | (2006.01) |

(52) U.S. Cl.
CPC ............ *C07D 243/12* (2013.01); *C07B 37/10* (2013.01); *C07C 231/02* (2013.01); *C07C 233/43* (2013.01); *C07B 2200/13* (2013.01)

(58) Field of Classification Search
CPC .... C07D 243/12; C07C 231/02; C07C 233/43
See application file for complete search history.

(56) References Cited

U.S. PATENT DOCUMENTS

| 3,984,398 A | 10/1976 | Rossi |
| 2003/0149027 A1† | 8/2003 | Oi |
| 2014/0357858 A1† | 12/2014 | Ushioda |

FOREIGN PATENT DOCUMENTS

| EP | 2597088 B1 † | 11/2017 |
| GB | 1 210 809 A | 11/1970 |
| GB | 1210809 A † | 11/1970 |
| GB | 1 214 662 A | 12/1970 |
| GB | 1 217 217 | 12/1970 |
| GB | 1214662 A † | 12/1970 |
| GB | 1 274 029 A | 5/1972 |
| GB | 1274029 A † | 5/1972 |
| IN | 259469 | 3/2014 |
| WO | 2011/100838 | 8/2011 |
| WO | 2011100838 A1 † | 8/2011 |

OTHER PUBLICATIONS

Yoshinobu Nakai, et al.; Study of the Interaction of Clobazam with Cyclodextrins in Solution and in the Solid State; Chemical & pharmaceutical bulletin 38 (3); 728-32 (1990); vol. 38, No. 3.
The claimed PXRD form is same as disclosed in chem pharma bull 1990, 38,728.†
Chem pharma bull 38, 728-732, 1990 this journal discloses pxrd of clobazam, which is same as claimed PXRD of US'939.†
Written Opinion of the ISA for PCT/IB2016/051562, dated Jun. 2, 2016.†
International Search Report for PCT/IB2016/051562, dated Jun. 2, 2016.†
H.J. Butcher, T.A. Hamor (1985)—Structure of 7-chloro-1-methyl-5-phenyl-1H-1,5-benzodiazepine-2,4(3H,5H)-dione (clobazam), C16H13ClN2O2. Acta Crystallographica, Section C: Crystal Structure Communications, 41, 1081-1083. DOI: 10.1107/S0108270185006667.†
International Preliminary Report on Patentability of PCT/IB2016/051562 dated Sep. 26, 2017.†

† cited by third party

*Primary Examiner* — Bruck Kifle
(74) *Attorney, Agent, or Firm* — Ladas & Parry LLP

(57) ABSTRACT

The present invention provides an improved process for the preparation of 8-chloro-1-phenyl-1H-benzo[b][1,4]diazepine-2,4(3H,5H)-dione (hereafter referred to as the compound (IV)), which is useful as a key intermediate for the synthesis of Clobazam (referred to as the compound (I)) 7-chloro-1-methyl-5-phenyl-1H-benzo[b][1,4]diazepine-2,4(3H,5H)-dione. The process of the present invention further involves transformation of the compound (IV) into Clobazam (I), comprising (a) reacting the compound (II) (as described herein) with monoalkyl malonate in the presence of a coupling agent to obtain the compound (III) (as described herein); followed by the cyclization using a base; (b) reacting the compound-IV (as described herein) obtained from step (a) with methylating agent. The process of the present invention involves formation of novel intermediates methyl 3-((4-chloro-2-(phenylamino)phenyl)amino)-3-oxopropanoate (IIIa) and 3-((4-chloro-2-(phenylamino)phenyl)amino)-3-oxopropanoic acid (V).

16 Claims, 1 Drawing Sheet

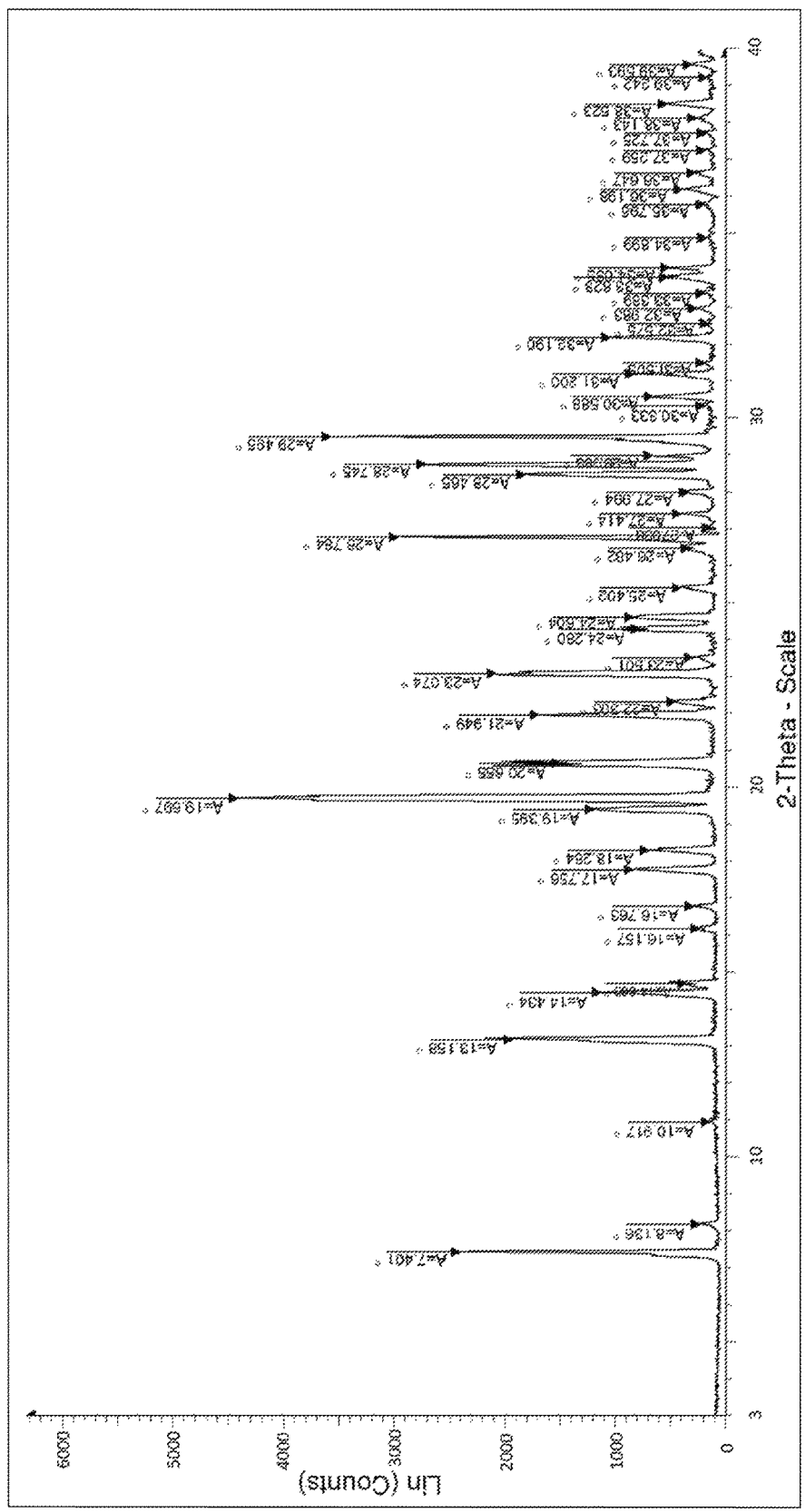

PROCESS FOR THE PREPARATION OF CLOBAZAM AND ITS INTERMEDIATE

RELATED APPLICATION

This application is a national phase entry under 35 USC 371 of International Patent Application No.: PCT/IB2016/051562 filed on 21 Mar. 2016, which claims priority from Indian Application No. 966/MUM/2015 filed on 24 Mar. 2015, the disclosures of which are incorporated in their entirety by reference herein.

FIELD OF THE INVENTION

The present invention relates to an improved process for the preparation of 8-chloro-1-phenyl-1H-benzo[b][1,4]diazepine-2,4(3H,5H)-dione (hereafter referred to as the compound (IV)), which is useful as a key intermediate for the synthesis of Clobazam (referred to as the compound (I)) 7-chloro-1-methyl-5-phenyl-1H-benzo[b][1,4]diazepine-2,4 (3H,5H)-dione. The process of the present invention further involves transformation of the compound (IV) into Clobazam (I).

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

Clobazam (the Compound (I)) is a psychotropic drug, essentially used for its anticonvulsant effects. The drug is marketed by LUNDBECK LLC under the trade name ONFI® in the form of oral tablets and oral suspension. ONFI is a benzodiazepine indicated for adjunctive treatment of seizures associated with Lennox-Gastaut syndrome (LGS) in patients 2 years of age or older. Clobazam is a 1,5-benzodiazepine, meaning that its diazepine ring has nitrogen atoms at the 1 and 5 positions (instead of the usual 1 and 4). Like other 1,5-benzodiazepines (e.g., arfendazam, lofendazam), it has less affinity for the ω1-allosteric binding site on the GABAA receptor compared to the 1,4-benzodiazepines. It has selective affinity for the ω2 site, where it has agonistic activity. Clobazam binds at a distinct binding site associated with a Cl-ionopore at the GABA-A receptor, increasing the duration of time for which the Cl-ionopore is open.

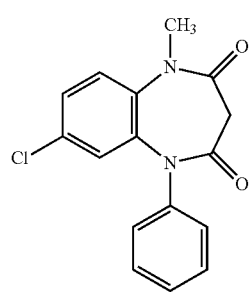

Compound (I)

Clobazam being an important drug for treatment and management of epilepsy and anxiety disorder; a number of processes for its preparation as well as for its intermediates are known in the art.

U.S. Pat. No. 3,984,398 (hereafter US'398) describe a process for the synthesis of Clobazam, which is illustrated below in Scheme-I. In the process, the compound, 5-chloro-2-nitro-N-phenylaniline is reacted with mono alkyl malonate to produce corresponding alkyl 3-((5-chloro-2-nitrophenyl) (phenyl)amino)-3-oxopropanoate which on further reduction converted to diamines compound. The patent US'398 describes the cyclization of alkyl 3-((2-amino-5-chlorophenyl) (phenyl) amino)-3-oxopropanoate in acid medium to obtain 8-chloro-1-phenyl-1H-benzo[b][1,4]diazepine-2,4(3H,5H)-dione (IV). It further describes the reaction of compound-IV with methyl halide to obtain 7-chloro-1-methyl-5-phenyl-1H-benzo[b][1,4]diazepine-2,4(3H,5H)-dione (I)

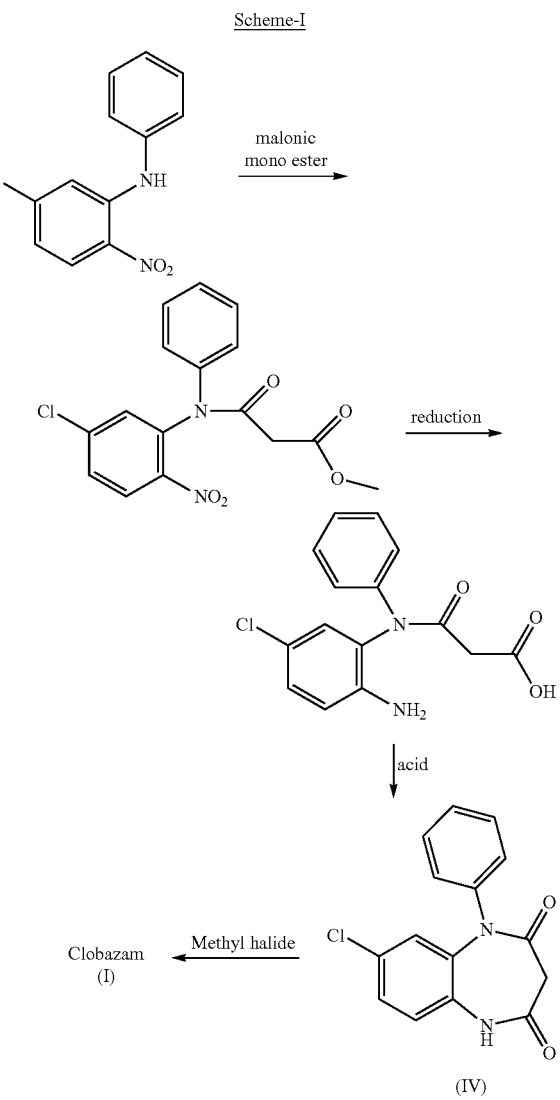

Scheme-I

GB patent no. 1217217 describe a process for the synthesis of Clobazam by the cyclization of 2-amino diphenylamine compound with Malonic acid dihalide and the obtained product compound (IV) is further methylated using methylating agent to obtain compound-1.

Indian patent 259469 (hereafter IN'469) describe a process for the synthesis of Clobazam (I) by the methylation of 8-chloro-1-phenyl-1H-benzo[b][1,4]diazepine-2,4(3H,5H)-dione (IV) using a methylating agent in an biphasic solvent system essentially in the presence of a phase transfer catalyst (PTC).

In addition to the afore discussed patent documents, there are a number of patent documents that describe a process for the preparation of similar compounds and Clobazam derivatives such as published PCT application WO-A-2011/100838, US patent application no. 2003/0149027, GB1274029 and GB1214662, Chemical & pharmaceutical bulletin 38 (3), 728-32 (1990).

It is evident from the discussion of the processes for the preparation of the 8-chloro-1-phenyl-1H-benzo[b][1,4]diazepine-2,4(3H,5H)-dione (IV), and further its conversion into the Clobazam (I), described in the afore cited prior art documents that some of the reported processes primarily provides product with low yield, which involve critical reaction conditions, biphasic reaction solvent system, use of complex reagents, purification using column chromatography and expensive solvents; which renders the process costlier and hence the processes are not industrially feasible.

In view of these drawbacks, there is a need to develop an industrially viable commercial process for the preparation of Clobazam and its intermediates; which is simple, efficient and cost-effective process and provides the desired compounds in improved yield and purity.

Inventors of the present invention have developed an improved process that addresses the problems associated with the processes reported in the prior art. The process of the present invention does not involve use of any toxic and/or costly solvents and reagents. Moreover, the process does not require additional purification steps and critical workup procedure. Accordingly, the present invention provides a process for the preparation of Clobazam and its intermediates, which is simple, efficient, cost effective, environmentally friendly and commercially scalable for large scale operations.

SUMMARY OF THE INVENTION

In one aspect, the present invention relates to an improved process for the preparation of Clobazam (I), comprising (a) reacting the compound (II) (as described herein) with monoalkyl malonate in the presence of a coupling agent to obtain the compound (III) (as described herein); followed by the cyclization using a base; (b) reacting the compound-IV (as described herein) obtained from step (a) with methylating agent.

In one aspect, the present invention relates to an improved process for the preparation of 8-chloro-1-phenyl-1H-benzo[b][1,4]diazepine-2,4(3H,5H)-dione (IV), comprising reacting the compound (II) (as described herein) with mono alkyl malonate in the presence of a coupling agent to obtain the compound (III) (as described herein); followed by the cyclization using a base.

In one aspect, the present invention relates to a novel intermediate compound methyl 3-((4-chloro-2-(phenylamino)phenyl)amino)-3-oxopropanoate (IIIa).

In one aspect, the present invention relates to an improved process for the preparation of methyl 3-((4-chloro-2-(phenylamino)phenyl)amino)-3-oxopropanoate (IIIa), comprising reacting the compound (II) (as described herein) with monoalkyl malonate in the presence of a coupling agent.

In one aspect, the present invention relates to an improved process for the preparation of Clobazam (I), comprising reacting the compound (IV) (as described herein) with dimethyl sulphate in the absence of a phase transfer catalyst.

In one aspect, the present invention relates to an improved process for the preparation of Clobazam (1), comprising (a-i) reacting the compound (II) (as described herein) with mono alkyl malonate in the presence of a coupling agent to obtain the compound (III) (as described herein); (b-i) hydrolyzing the compound (III) obtained from step (a) to corresponding acid compound (V); (c-i) cyclizing the compound (V) to obtain compound (IV); (d-i) reacting the compound-IV (as described herein) obtained from step (c) with methylating agent.

In one aspect, the present invention relates to an improved process for the preparation of 8-chloro-1-phenyl-1H-benzo[b][1,4]diazepine-2,4(3H,5H)-dione (IV), comprising (a) reacting the compound (II) (as described herein) with monoalkyl malonate in the presence of a coupling agent to obtain the compound (III) (as described herein); (b) hydrolyzing the compound (III) obtained from step (a) to corresponding acid compound (V); followed by the cyclization.

In an embodiment, there is provided a novel intermediate compound as 3-((4-chloro-2-(phenylamino)phenyl)amino)-3-oxopropanoic acid (V).

In another aspect, the present invention provides a novel crystalline Form-P of Clobazam; characterized by the X-ray powder diffraction graph as FIG. 1 and Table-1.

DESCRIPTION OF THE FIGURES

FIG. 1: X-ray Powder Diffraction (XRPD) pattern of the crystalline Form-P of Clobazam.

DETAILED DESCRIPTION OF THE INVENTION

Accordingly, the present invention relates to an improved process for the preparation of 7-chloro-1-methyl-5-phenyl-1H-benzo[b][1,4]diazepine-2,4(3H,5H)-dione (I) represented by the following formula,

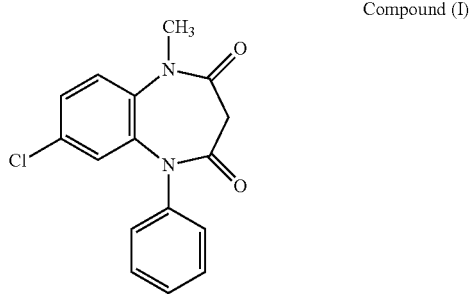 [SMILES: CN1C(=O)CC(=O)N(c2ccccc2)c2cc(Cl)ccc21]

Compound (I)

comprising the steps of
(a) preparation of alkyl 3-((4-chloro-2-(phenylamino)phenyl)amino)-3-oxopropanoate (III), represented by the following formula:

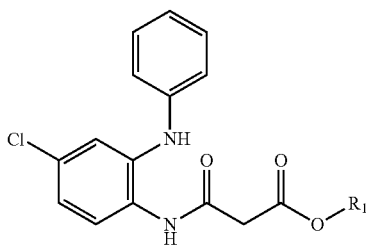

wherein $R_1$ is $C_1$-$C_{10}$ alkyl.

by reacting the compound (II) represented by the following formula;

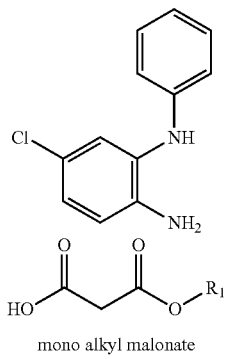

mono alkyl malonate

With mono alkyl malonate in the presence of a coupling agent;

(b) preparation of 8-chloro-1-phenyl-1H-benzo[b][1,4]diazepine-2,4(3H,5H)-dione (IV), represented by the following formula;

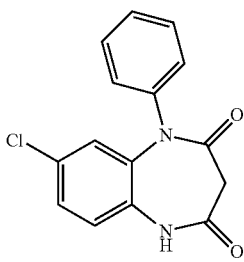

by cyclization of compound (III) obtained from step (a) in the presence of a base;

(c) reacting the compound (IV) obtained from step (b) with a methylating agent.

In the context of the present invention, the term 'coupling agent' used in reference to any reagent or compound used in the reaction to improve the condensation or coupling of compounds.

Accordingly, in the process of the present invention the intermediate compound (III) is optionally isolated during reaction, or in-situ converted to compound (IV).

In the context of the present invention, the term "optionally" when used in reference to any element; including a process step e.g. isolation of a compound; it is intended to mean that the subject element is isolated, or alternatively, is not isolated before transformation into the further compound. Both alternatives are intended to be within the scope of the present invention In an embodiment, the 'coupling agent' is selected from the group consisting of dicyclohexyl-carbodiimide, diethyl cyanophosphate, 1-ethyl-3-(3-dimethylaminopropyl) carbodiimide.

In an embodiment, the 'methylating agent' is selected from the group consisting methyl iodide, dimethyl sulphate.

Accordingly, in an embodiment the present invention relates to a process for the preparation of Clobazam (I) represented by the following formula,

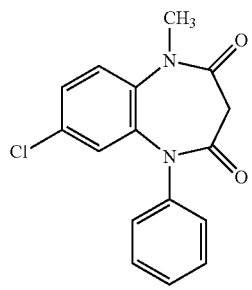

Compound (I)

comprising the steps of (d) preparation of methyl 3-((4-chloro-2-(phenylamino)phenyl)amino)-3-oxopropanoate (IIIa), represented by the following formula;

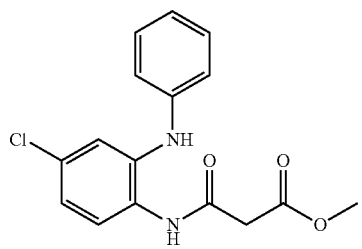

by reacting the compound (II) represented by the following formula;

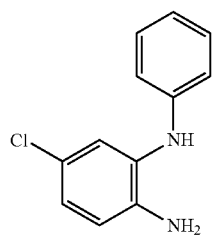

With monomethyl malonate in the presence of a dicyclohexylcarbodiimide (DCC);

(e) preparation of 8-chloro-1-phenyl-1H-benzo[b][1,4]diazepine-2,4(3H,5H)-dione (IV), represented by the following formula;

IV

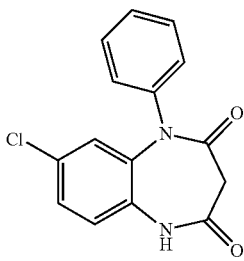

by cyclization of compound (III) obtained from step (a) in the presence of a base;
(f) reacting the compound (IV) obtained from step (b) with dimethyl sulphate.

In an embodiment, the base is selected from potassium tert-butoxide or sodium tert-butoxide.

In an embodiment, the methylation step is carried in the absence of a Phase transfer catalyst.

In a specific embodiment, the process for the preparation of 7-chloro-1-methyl-5-phenyl-1H-benzo[b][1,4]diazepine-2,4(3H,5H)-dione (I) comprises the steps of:
(1) dissolving the compound-II in a solvent;
(2) adding the monomethyl malonate and a coupling agent to the reaction mixture of step (1);
(3) stirring the reaction mixture of step (2) at room temperature;
(4) optionally, isolating the product compound (III) of step (3);
(5) adding a base to the stirring solution of step-(4);
(6) optionally, isolating the product compound (IV) of step (5);
(7) adding a methylating agent to the stirring solution of step-(6);
(8) isolating the desired product.

The process of the present invention as per the specific embodiment described above is illustrated in the following Scheme-II, Scheme-II

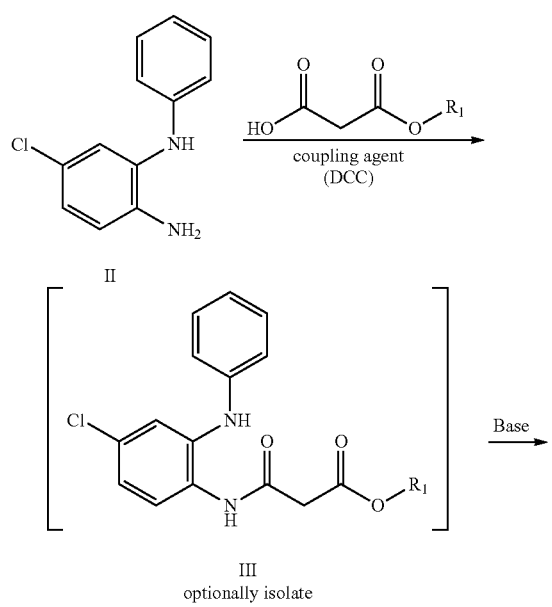

II

III
optionally isolate

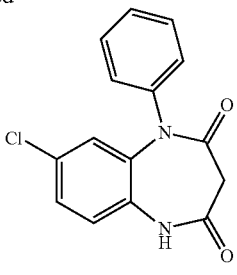

IV methylating agent
(Dimethyl sulphate)

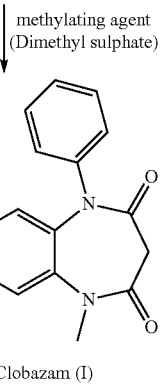

Clobazam (I)

The solvent used in the step-(1) to step-(8) of the above process (as depicted in the Scheme II) is selected from the halogenated solvent such as dichloromethane, 4-bromotoluene, diiodomethane, carbon tetrachloride, chlorobenzene and chloroform; alcoholic solvent such as methanol, ethanol, isopropanol, t-amyl alcohol, t-butyl alcohol and hexanol; an ether solvent such as tetrahydrofuran, cyclopentyl methyl ether, 2-methyltetrahydrofuran, diethyl ether and 1,4-dioxane; a ketone selected from methyl ethyl ketone, acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; acetone; water or a mixture thereof The coupling agent used in the step-(2) of the above process (as depicted in the Scheme II) is selected from the dicyclohexylcarbodiimide (DCC), diethyl cyanophosphate, 1-ethyl-3-(3-dimethylaminopropyl) carbodiimide.

The term 'isolating the desired' referred to in the step (4), step (6) and step (8) corresponds to the steps involving biphasic separation, separation of organic phase, filtration, evaporation of solvent, cooling, precipitation, washing and drying.

In the context of the present invention step (4) and step (6), the term "optionally" when used in reference to any element; including a process step e.g. isolation of a compound; it is intended to mean that the subject element is isolated, or alternatively, is not isolated before transformation into the further compound. Both alternatives are intended to be within the scope of the present invention The base used in the step-(5) of the above process (as depicted in the Scheme II) is selected from the group consisting of potassium tert-butoxide, sodium tert-butoxide, alkoxy base wherein alkyl containing $C_1$-$C_{10}$.

The methylating agent used in the step-(7) of the above process (as depicted in the Scheme II) is selected from the group consisting methyl iodide, dimethyl sulphate, methyl halide.

The overall process of the present invention involving preparation of Clobazam (I) via formation of intermediate compound (III) is illustrated in the following Scheme III:

Scheme-III

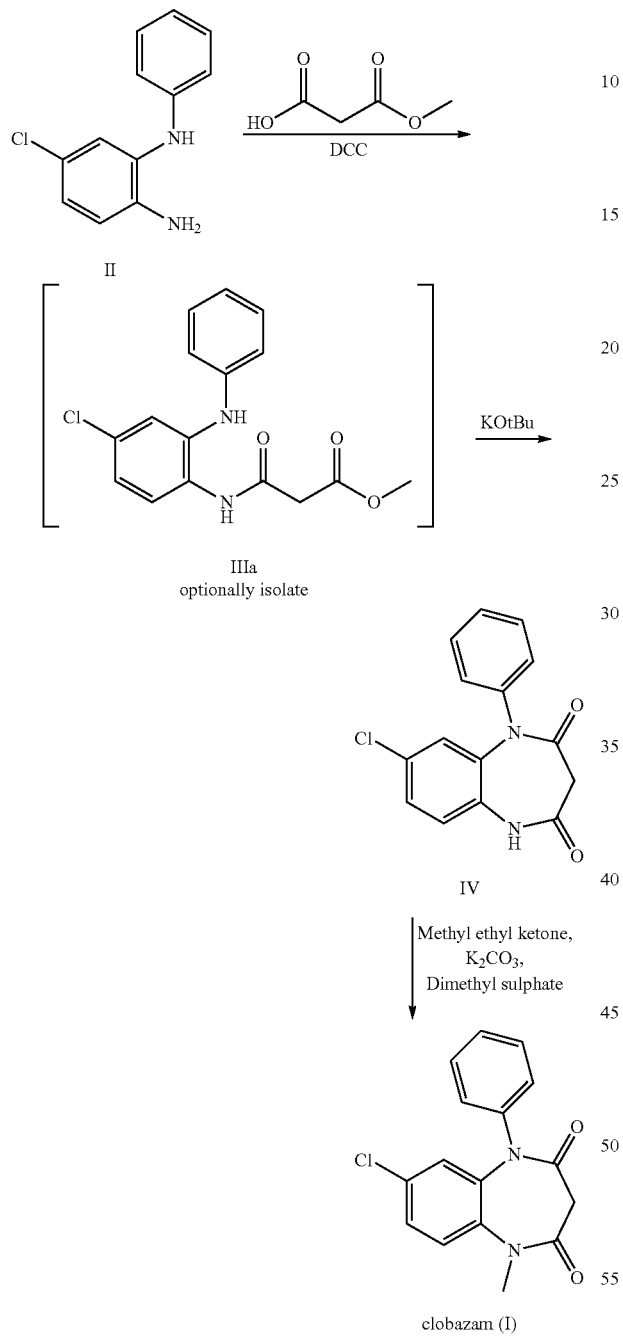

clobazam (I)

The process illustrated in the above Scheme III comprises reaction of the compound (II) with monomethyl malonate in the presence of a coupling agent selected for DCC to obtain compound (IIIa). After completion of the reaction, the product compound (IIIa) was treated with a base selected from potassium tert-butoxide to obtain the compound (IV). The cyclized compound (IV) was treated with a methylating agent selected from dimethyl sulphate and stirred at a higher temperature of about 50° C. The organic layer was separated to obtain desired product with about 80% yield with about 96% HPLC purity.

In an embodiment, there is provided an a novel intermediate compound as methyl 3-((4-chloro-2-(phenylamino)phenyl)amino)-3-oxopropanoate (IIIa).

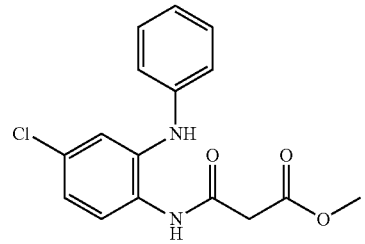

In an embodiment, there is provided an improved process for the preparation of 8-chloro-1-phenyl-1H-benzo[b][1,4]diazepine-2,4(3H,5H)-dione (IV), wherein the compound-IV has HPLC purity as ≥99.8%.

According to yet another aspect, the present invention relates to an improved process for the preparation of 7-chloro-1-methyl-5-phenyl-1H-benzo[b][1,4]diazepine-2,4(3H,5H)-dione (I) represented by the following formula,

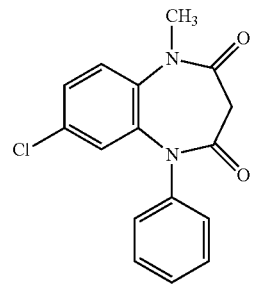

comprising the steps of (a-i) preparation of alkyl 3-((4-chloro-2-(phenylamino)phenyl)amino)-3-oxopropanoate (III), represented by the following formula;

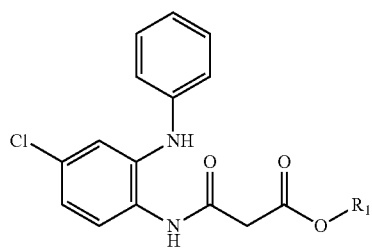

wherein $R_1$ is $C_1$-$C_{10}$ alkyl.

by reacting the compound (II) represented by the following formula;

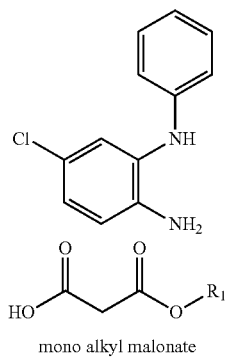

with mono alkyl malonate in the presence of a coupling agent;

(b-i) preparation of 3-((2-amino-5-chlorophenyl)(phenyl) amino)-3-oxopropanoic acid (V), represented by the following formula;

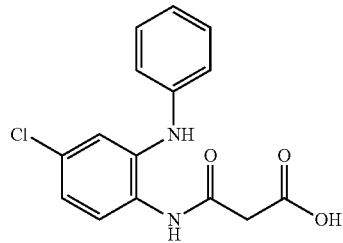

by hydrolysis of compound (III) obtained from step (a-i) using a base:

(c-i) preparation of 8-chloro-1-phenyl-1H-benzo[b][1,4]diazepine-2,4(3H,5H)-dione (IV), represented by the following formula;

by cyclization of compound (V) obtained from step (b-i) in the presence of a cyclizing agent:

(d-i) reacting the compound (IV) obtained from step (c-i) with a methylating agent.

In the context of the present invention, the term 'coupling agent' used in reference to any reagent or compound used in the reaction to improve the condensation or coupling of compounds.

In the context of the present invention, the term 'cyclizing agent' used in reference to any reagent or compound used in the reaction to improve the condensation or coupling of compounds. The 'cyclizing agent' can be same as coupling agent or a base.

Accordingly, in the process of the present invention the intermediate compound (III) is optionally isolated during reaction, or in-situ converted to compound (IV).

In the context of the present invention, the term "optionally" when used in reference to any element; including a process step e.g. isolation of a compound; it is intended to mean that the subject element is isolated, or alternatively, is not isolated before transformation into the further compound. Both alternatives are intended to be within the scope of the present invention In an embodiment, the 'coupling agent and/or cyclizing agent' is selected from the group consisting of dicyclohexylcarbodiimide, diethyl cyanophosphate, 1-ethyl-3-(3-dimethylamino propyl) carbodiimide.

In an embodiment, the 'methylating agent' is selected from the group consisting methyl iodide, dimethyl sulphate.

In an embodiment, the 'base' used for hydrolysis is selected from the group consisting sodium hydroxide, potassium hydroxide, alkali hydroxide.

In an another specific embodiment, the process for the preparation of 7-chloro-1-methyl-5-phenyl-1H-benzo[b][1,4]diazepine-2,4(3H,5H)-dione (I) comprises the steps of:

(i) dissolving the compound (II) in a solvent;
(ii) adding the monomethyl malonate and a coupling agent to the reaction mixture of step (i);
(iii) stirring the reaction mixture of step (ii) at room temperature;
(iv) optionally, isolating the product compound (III) of step (iii);
(v) hydrolyzing compound (III) of step (iv) by adding a base to the stirring solution of step-(iv);
(vi) optionally, isolating the product compound (V) of step (v);
(vii) adding coupling agent to the stirring solution of step (vi);
(viii) optionally, isolating the product compound (IV) of step (vii);
(ix) adding a methylating agent to the stirring solution of step-(viii);
(x) isolating the desired product.

The process of the present invention as per the specific embodiment described above is illustrated in the following Scheme-IV, Scheme-IV

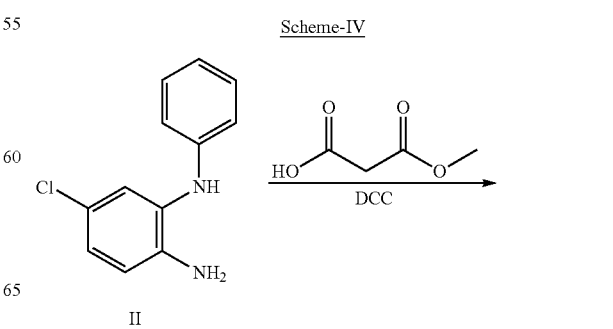

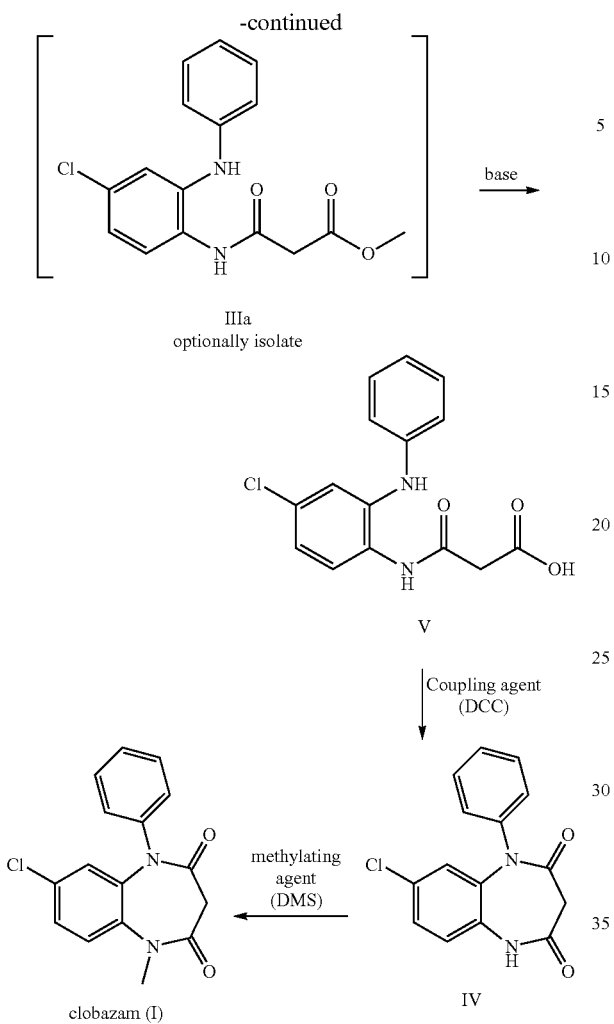

clobazam (I)

The solvent used in the step-(i) to step-(x) of the above process (as depicted in the Scheme IV) is selected from the halogenated solvent such as dichloromethane, 4-bromotoluene, diiodomethane, carbon tetrachloride, chlorobenzene and chloroform; alcoholic solvent such as methanol, ethanol, isopropanol, t-amyl alcohol, t-butyl alcohol and hexanol; an ether solvent such as tetrahydrofuran, cyclopentyl methyl ether, 2-methyltetrahydrofuran, diethyl ether and 1,4-dioxane; a ketone selected from methyl ethyl ketone, acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; acetone; water or a mixture thereof.

The coupling agent used in the step-(ii) and step-(vii) of the above process (as depicted in the Scheme IV) is selected from the dicyclohexylcarbodiimide (DCC), diethyl cyanophosphate, 1-ethyl-3-(3-dimethylaminopropyl) carbodiimide.

The term 'isolating the desired' referred to in the step (iv), step (vi), step (viii) and step (x) corresponds to the steps involving biphasic separation, separation of organic phase, filtration, evaporation of solvent, cooling, precipitation, washing and drying.

In the context of the present invention step (iv), step (vi) and step (viii), the term "optionally" when used in reference to any element; including a process step e.g. isolation of a compound; it is intended to mean that the subject element is isolated, or alternatively, is not isolated before transformation into the further compound. Both alternatives are intended to be within the scope of the present invention.

The base used in the step-(v) of the above process (as depicted in the Scheme IV) is selected from the group consisting of potassium hydroxide, sodium hydroxide, alkali hydroxide.

The methylating agent used in the step-(ix) of the above process (as depicted in the Scheme IV) is selected from the group consisting methyl iodide, dimethyl sulphate, methyl halide.

The process illustrated in the above Scheme IV comprises reaction of the compound (II) with monomethyl malonate in the presence of a coupling agent selected for DCC to obtain compound (IIIa). After completion of the reaction, the product compound (IIIa) was hydrolyzed by treated with a base selected from sodium hydroxide to obtain the acid compound (V). The acid compound (V) was treated with a coupling agent selected for DCC to obtain cyclized compound IV. The cyclized compound (IV) was treated with a methylating agent selected from dimethyl sulphate and stirred at a higher temperature of about 50° C., the organic layer was separated to obtain desired product with about 80% yield with about 96% HPLC purity.

In an embodiment, there is provided an a novel intermediate compound as 3-((4-chloro-2-(phenylamino)phenyl)amino)-3-oxopropanoic acid (V);

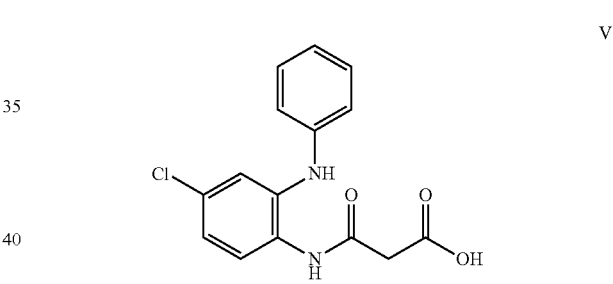

V

It is further evident that, the process reported in the prior art for methylation using dimethyl sulphate involves biphasic solvent system essentially in the presence of a phase transfer catalyst.

The use of bibasic solvent system and PTC renders the reaction procedure costlier with tedious and complex work up steps. Advantageously, the process of present invention is simpler and it overcomes the drawbacks of the known methods.

Advantageously, the process of present invention provides product with significant improvements in the purity and yield over the processes reported in the prior art. Hence the process of the instant invention effectively contributes to the reduction of overall cost of the process.

According to yet another aspect, the present invention provides a novel crystalline Form-P of Clobazam.

In an embodiment, the crystalline Form-P of Clobazam is characterized by an XRPD pattern having peaks at 7.4, 13.2, 14.4, 17.7, 18.3, 19.3, 19.6, 20.6, 21.9, 22.3, 23.0, 24.2, 24.6, 26.7, 28.4, 28.7, 28.9, 29.4, 30.5, 31.2, 32.1, 33.8, 34.0 and 38.5±0.2 degrees 2θ.

In an embodiment, the crystalline Form-P of Clobazam is further characterized by the X-ray powder diffraction graph as FIG. 1.

In an embodiment, the crystalline Form-P of Clobazam is further characterized by the X-ray powder diffraction graph having d-spacing values as per Table-1.

The X-ray powder diffraction spectrum of Clobazam was measured under the following experimental conditions;
Instrument: X-Ray Diffractometer, Bruker D8 Advance
X-Ray: Cu/40 kv/40 mA
Diverging: 0.3°
Counter: Lynx Eye
Scan Mode: Continuous
Scan Axes: Two Theta/Theta
Scan Range: 3° to 40°
Generator power: 40 kV, 40 mA
Scan range: 3-40° 2 θ
Step size: 0.02°
Step time 0.25 sec
Sample rotation: 15 rpm
Detector: Lynx-Eye

TABLE 1 summarizes the d-spacing values in °A, and the corresponding 2θ values of the crystalline Form-P of Clobazam.
Form-P Clobazam

| Angle 2-Theta ° | d-spacing value Angstrom | Intensity % |
|---|---|---|
| 7.401 | 11.93498 | 54.4 |
| 8.136 | 10.85829 | 4.9 |
| 10.917 | 8.09793 | 2.9 |
| 13.158 | 6.72347 | 43.6 |
| 14.434 | 6.13176 | 25.4 |
| 14.66 | 6.03773 | 7.8 |
| 16.157 | 5.4813 | 5 |
| 16.763 | 5.28451 | 6.1 |
| 17.756 | 4.99121 | 18.7 |
| 18.284 | 4.84837 | 15.5 |
| 19.395 | 4.57298 | 26.7 |
| 19.697 | 4.5035 | 100 |
| 20.655 | 4.2967 | 33.7 |
| 21.949 | 4.0463 | 38.1 |
| 22.303 | 3.98282 | 10 |
| 23.074 | 3.85143 | 47 |
| 23.501 | 3.78253 | 6.4 |
| 24.28 | 3.66284 | 17.3 |
| 24.604 | 3.6153 | 18.6 |
| 25.402 | 3.50359 | 8.8 |
| 26.482 | 3.36303 | 7.1 |
| 26.784 | 3.32585 | 67.1 |
| 27.038 | 3.29515 | 2.8 |
| 27.414 | 3.25075 | 8.8 |
| 27.994 | 3.1847 | 7.3 |
| 28.465 | 3.13309 | 40.9 |
| 28.745 | 3.10319 | 61.3 |
| 28.983 | 3.07826 | 14.7 |
| 29.495 | 3.02603 | 80.9 |
| 30.333 | 2.94429 | 4 |
| 30.588 | 2.92032 | 14.6 |
| 31.2 | 2.86441 | 18.5 |
| 31.505 | 2.8374 | 4.1 |
| 32.19 | 2.77853 | 23.4 |
| 32.575 | 2.74661 | 3.2 |
| 32.983 | 2.71354 | 5.5 |
| 33.389 | 2.68146 | 4 |
| 33.828 | 2.64766 | 11.5 |
| 34.085 | 2.62831 | 11.2 |
| 34.899 | 2.56886 | 3.6 |
| 35.795 | 2.50657 | 4 |
| 36.198 | 2.47954 | 8.5 |
| 36.647 | 2.45019 | 5.8 |
| 37.259 | 2.41135 | 3.9 |
| 37.725 | 2.38264 | 3.8 |
| 38.143 | 2.35748 | 5.7 |
| 38.523 | 2.3351 | 11.7 |
| 39.242 | 2.29395 | 3.5 |
| 39.593 | 2.27444 | 6.6 |

In an embodiment, the crystalline Form-P of Clobazam in obtained by the following general procedure:
(s) suspending/dissolving Clobazam in a solvent,
(t) heating the reaction mixture of step (s) at reflux temperature,
(u) cooling the reaction mixture of step (t) to a lower temperature of about 15- 25° C, and
(v) isolating the precipitated solid.

In an embodiment, the solvent used in the step-(s) is selected from the halogenated hydrocarbon, aromatic hydrocarbon, an alcohol, an ether solvent, an ester, a ketone, a nitrile, an amide, a sulfoxide, a lactam, water; or a mixture thereof.

The solvent used in the step-(s) is selected from the halogenated solvent such as dichloromethane, 4-bromotoluene, diiodomethane, carbon tetrachloride, chlorobenzene and chloroform; alcoholic solvent such as methanol, ethanol, isopropanol, t-amyl alcohol, t-butyl alcohol and hexanol; an ether solvent such as tetrahydrofuran, cyclopentyl methyl ether, 2-methyltetrahydrofuran, diethyl ether and 1,4-dioxane; a ketone selected from methyl ethyl ketone, acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; acetone; water or a mixture thereof.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1

Preparation of 8-chloro-1-phenyl-1H-benzo[b][1,4] diazepine-2,4(3H,5H)-dione (IV)

Charged 900 mL of Toluene in a flask followed by the addition of dimethyl formamide (100 mL) and compound (II) (100 g). To the stirring solution was added DCC (110 g) and monomethyl malonate (60 g). The reaction mixture was cooled to a temperature about 15° C. and was added potassium tert-butoxide (60 g). The reaction mixture was stirred at temperature about 40° C. and organic layer was separated by adding water at pH (6.5 to 8). The residue was treated with acetone to obtain desired compound (yield: 80%, purity≥99% HPLC).

Example-2

Preparation of Clobazam (I)

Charged 600 ml Methyl Ethyl Ketone in a flask followed by the addition of compound (IV) (100 g), potassium carbonate (145 g) and dimethyl sulphate (90 g). The reaction mixture was stirred at temperature 50° C. and organic layer was separated by adding water (300 ml), the combined organic layer was evaporated and residue treated with IPA to get desired product. (yield: 75%, purity≥99.5% HPLC).

Example-3

Preparation of 3-((2-amino-5-chlorophenyl)(phenyl)amino)-3-oxopropanoic acid (V)

Charged 300 ml of dimethyl formamide in a flask followed by the addition of compound (II) (100 gm), DCC (108 g) and monomethyl malonate (155 ml). The reaction mixture was stirred at temperature about 30° C. The reaction mixture was quenched with water. The residue was dissolved in methanol (600 ml) and was treated with aq. Sodium hydroxide solution (625 ml). The crude was treated with conc. hydrochloric acid (200 ml) to obtain desired product. (Purity≥98% HPLC).

Example-4

Preparation of Crystalline Form-P of Clobazam 50 g of Clobazam was dissolved in dichloromethane (150 mL) in a RBF. To the stirring solution was added charcoal (5 g) and stirred for 30 min at room temperature. The reaction mixture was filtered and solvent evaporated till volume remains to 50-65 mL. To the residue was added 450 mL of isopropyl alcohol and refluxed for 30 min. The reaction mixture was cooled to 15-25° C. and precipitated product was filtered to obtain crystalline product with yield: 47 g.

We claim:

1. A process for the preparation of Clobazam (compound-I) of the following formula,

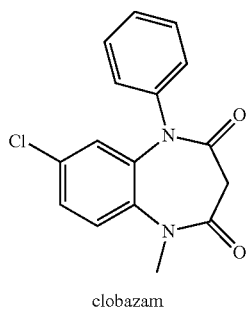

clobazam comprising the steps;

(a) reacting 5-chloro-$N^1$-phenylbenzene-1,2-diamine (II) of the following formula with mono alkyl malonate in the presence of a coupling agent; to obtain alkyl 3-((4-chloro-2-(phenylamino)phenyl)amino)-3-oxopropanoate (III);

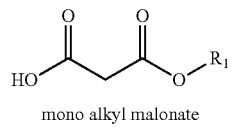

mono alkyl malonate

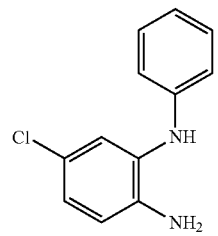

II

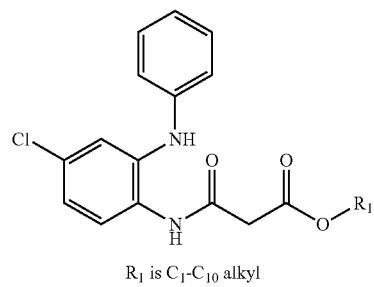

III $R_1$ is $C_1$-$C_{10}$ alkyl wherein, the compound (III) is optionally isolated, (b) cyclizing the compound (III) of step (a) in the presence of a base to obtain 8-chloro-1-phenyl-1H-benzo[b][1,4]diazepine-2,4(3H,5H)-dione (IV) of the following formula;

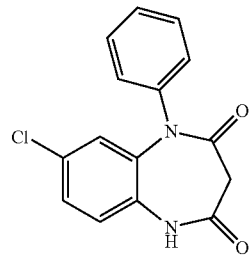

IV (c) reacting the compound (IV) obtained from step (b) with a methylating agent.

2. The process according to claim 1, wherein the base used in step (b) is selected from the group consisting of metal alkoxide selected from potassium tert-butoxide or sodium tert-butoxide.

3. A process for the preparation of Clobazam (compound-I) of the following formula,

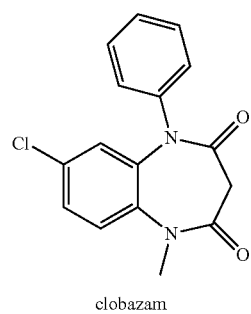

clobazam comprising the steps;

(a-i) reacting 5-chloro-$N^1$-phenylbenzene-1,2-diamine (II) of the following formula with mono alkyl malonate in the presence of a coupling agent; to obtain alkyl 3-((4-chloro-2-(phenylamino)phenyl)amino)-3-oxopropanoate (III);

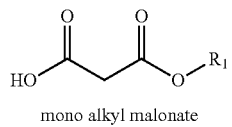

mono alkyl malonate

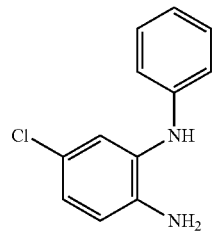

II

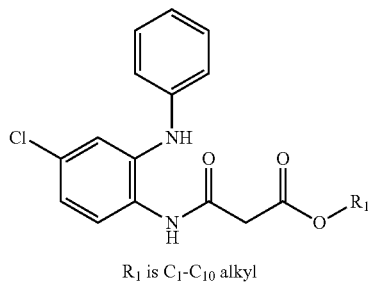

III $R_1$ is $C_1$-$C_{10}$ alkyl wherein, the compound (III) is optionally isolated, (b-i) hydrolyzing the compound (III) obtained from step (a-i) using a base, to obtain 3-((4-chloro-2-(phenylamino)phenyl)amino)-3-oxopropanoic acid (V) of the following formula;

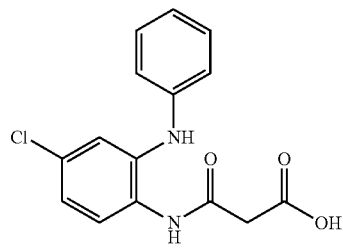

V (c-i) cyclizing the compound (V) of step (b-i) in the presence of a coupling agent to obtain 8-chloro-1-phenyl-1H-benzo[b][1,4]diazepine-2,4(3H,5H)-dione (IV) of the following formula;

IV (d-i) reacting the compound-IV obtained from step (c-i) with a methylating agent.

4. The process according to claim 1, wherein the mono alkyl malonate used in step (a) of claims 1 is a $C_1$-$C_{10}$ mono alkyl malonate.

5. The process according to claim 1, wherein the coupling agent used in step (a) of claim 1 is selected from the group consisting of dicyclohexylcarbodiimide (DCC), diethyl cyanophosphate and 1-ethyl-3-(3-dimethylaminopropyl) carbodiimide.

6. The process according to claim 1, wherein the methylating agent used in step (c) of claim 1 is selected from methyl iodide or dimethyl sulphate.

7. The process according to claim 1, wherein the methylation step (c) of claim 1 is in the absence of a phase transfer catalyst.

8. The process according to claim 3, wherein the base used in step (b-i) is an alkali hydroxide selected from potassium hydroxide or sodium hydroxide.

9. A compound: methyl 3-((4-chloro-2-(phenylamino)phenyl)amino)-3-oxopropanoate (IIIa) of following formula;

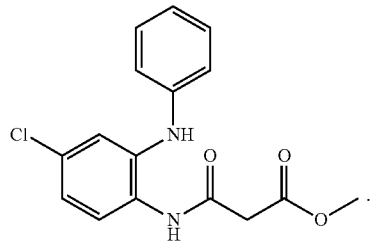

IIIa

10. A compound: 3-((4-chloro-2-(phenylamino)phenyl)amino)-3-oxopropanoic acid (V) of following formula;

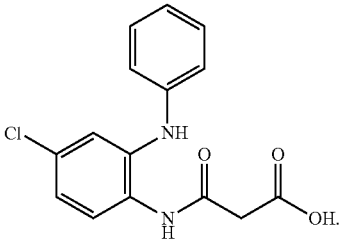

V

11. A crystalline Form-P of Clobazam, characterized by an XRPD pattern having peaks at 7.4, 13.2, 14.4, 17.7, 18.3, 19.3, 19.6, 20.6, 21.9, 22.3, 23.0, 24.2, 24.6, 26.7, 28.4, 28.7, 28.9, 29.4, 30.5, 31.2, 32.1, 33.8, 34.0 and 38.5 ±0.2 degrees 2θ.

12. A process for preparation of the crystalline Form-P of Clobazam according to claim 11, comprising the steps of;
   (s) suspending/dissolving Clobazam in a halogenated hydrocarbon solvent,
   (t) heating the reaction mixture of step (s) at reflux temperature,
   (u) cooling the reaction mixture of step (t) to a lower temperature of about 15-25° C., and
   (v) isolating the precipitated solid.

13. The process according to claim 3, wherein the mono alkyl malonate used in step (a-i) of claim 3 is a $C_1$-$C_{10}$ mono alkyl malonate.

14. The process according to claim 3, wherein the coupling agent used in step (a-i) of claim 3 or step (c-i) of claim 3 is selected from the group consisting of dicyclohexylcarbodiimide (DCC), diethyl cyanophosphate and 1-ethyl-3-(3-dimethylaminopropyl) carbodiimide.

15. The process according to claim 3, wherein the methylating agent used in step (d-i) of claim 3 is selected from methyl iodide or dimethyl sulphate.

16. The process according to claim 3, wherein the methylation step (d-i) of claim 3 is in the absence of a phase transfer catalyst.

* * * * *